US006846497B2

United States Patent
Okoniewska et al.

(10) Patent No.: US 6,846,497 B2
(45) Date of Patent: Jan. 25, 2005

(54) RAPIDLY EXPANDING STARCHES WITH ALTERED CRYSTALLINE STRUCTURE

(75) Inventors: Monika K. Okoniewska, Princeton, NJ (US); James J. Kasica, Whitehouse Station, NJ (US); Eric M. Weisser, Somerset, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 12 days.

(21) Appl. No.: 10/354,714

(22) Filed: Jan. 30, 2003

(65) Prior Publication Data

US 2004/0151767 A1 Aug. 5, 2004

(51) Int. Cl.[7] ........................ A61K 9/48; A61K 31/718; C08B 31/00
(52) U.S. Cl. ........................ 424/464; 536/102; 536/105; 536/106; 536/111; 514/60
(58) Field of Search ............................... 536/102, 105, 536/106, 111; 514/60; 424/464

(56) References Cited

U.S. PATENT DOCUMENTS

| 3,034,911 A | 5/1962 | McKee et al. |
|---|---|---|
| 3,490,742 A | 1/1970 | Nichols et al. |
| 3,622,677 A | 11/1971 | Short et al. |
| 4,369,308 A | 1/1983 | Trubiano |
| 4,383,111 A | 5/1983 | Takeo et al. |
| 4,447,601 A | 5/1984 | Takeo et al. |
| 5,468,286 A | 11/1995 | Wai-Chiu et al. |
| 5,616,343 A | 4/1997 | Cartilier et al. |
| 5,807,575 A | 9/1998 | Dumoulin et al. .......... 424/464 |
| 5,830,884 A | 11/1998 | Kasica et al. |
| 6,143,324 A | 11/2000 | Michaud et al. |
| 6,231,675 B1 | 5/2001 | Chiu et al. .................... 127/67 |
| 6,299,907 B1 | 10/2001 | Seib et al. |
| 2001/0003619 A1 | 6/2001 | Lefevre et al. ........ 428/402.24 |

FOREIGN PATENT DOCUMENTS

| WO | WO 96/22110 A3 | 7/1996 | .......... A61K/47/36 |
|---|---|---|---|
| WO | WO 96/22110 A2 | 7/1996 | .......... A61K/47/36 |
| WO | WO 02/02084 | 1/2002 | ............ A61K/9/20 |

*Primary Examiner*—James D. Wilson
*Assistant Examiner*—Everett White
(74) *Attorney, Agent, or Firm*—Karen G. Kaiser

(57) ABSTRACT

This invention relates to a starch based tablet disintegrant useful at low addition levels and providing equally effective properties in water and physiological fluids. The starches are characterized by their low solubility in cold water, high swelling power and labile birefringence in the dry state, which rapidly disappears upon addition of water. The preferred starches are inhibited then processed to remove a portion of the granular structure.

17 Claims, 3 Drawing Sheets

RAPIDLY EXPANDING STARCHES WITH ALTERED CRYSTALLINE STRUCTURE

FIELD OF THE INVENTION

The present invention relates to starches capable of undergoing rapid, irreversible swelling on hydration with water or physiological solutions. The starch derivatives of this invention are unique in that at least some crystallinity in the granular structure remains before hydration, yet are able to swell at room temperature when water is added. Additionally, these starches swell to the same relative degree regardless of ionic strength of the water solution. This is critical in predicting the hydration extent in various concentrations of salt such as physiological solutions.

SUMMARY OF THE INVENTION

The present invention relates to a starch based super-disintegrant for tablet applications. Disintegrants perform by rapidly swelling and applying force to disrupt the tablet structure and are generally used at about 5 to 10 percent dry basis of the total tablet weight. Super-disintegrants work by the same mechanism, but are more effective and are typically used at or below about 1 percent.

Inhibited starches that have been fully pregelatinized and used for tablet disintegrants are described in U.S. Pat. No. 4,369,308 to Trubiano. While these starches provide good disintegration properties, they are used at fairly high levels and have the associated issues with relatively high level of solubles. If during the swelling, the particles become sticky or soluble they will interfere with the release of the active material (e.g. pharmaceutical material). Particles with very limited swelling will not provide sufficient force to cause the tablet to rupture and release it's content.

Carboxymethyl starches (CMS, and other highly charged starch derivatives), described in U.S. Pat. No. 3,034,911 to McKee et al. for use as tablet disintegrants, are effective because of their excellent swelling power. The swelling of these pregelatinized, highly charged starches, like CMS, are highly susceptible to salt concentration and tend to display reduced swelling in salt solution. Ideally, disintegrants should provide similar swelling capacity in all types of media, primarily in water and physiologically fluids (e.g. stomach acids). Additionally, these materials have high levels of solubles, which interfere with their ability to function as disintegrants.

According to U.S. Pat. No. 6,143,423 issued to Michaud et al. the combination of a non-swollen birefringent granules and partially swollen non-birefringent granules provide disintegration in addition to good binding properties. A swollen granule of at least 50% of the original size marks the non-birefringent starches disclosed in this reference. The effectiveness of the disclosed mixture is reduced because the native birefringent granules provide little or no disintegration power.

Non-birefringent granules with residual shell film structure are described in U.S. Pat. Nos. 4,447,601 and 4,383,111, issued to Takeo et al. in which all the crystallinity is lost and the resulting starch is amorphous. Takeo states that low solubility (less than about 10%) is important to the effectiveness of the disintegrant. The starches disclosed in this reference are not chemically or physically modified, therefore their efficiency is limited by the amount of cold water soluble material in native starch. This is of particular importance for charged starches such as potato (a root starch), which would typically exhibit higher levels of cold water soluble components without chemical or physical intervention.

Thus, there is still a need in the current market for a safe, natural and effective disintegrant that will function at low usage levels and provide rapid tablet disintegration in all types of aqueous systems.

DETAILED DESCRIPTION OF THE INVENTION

Figure 1:
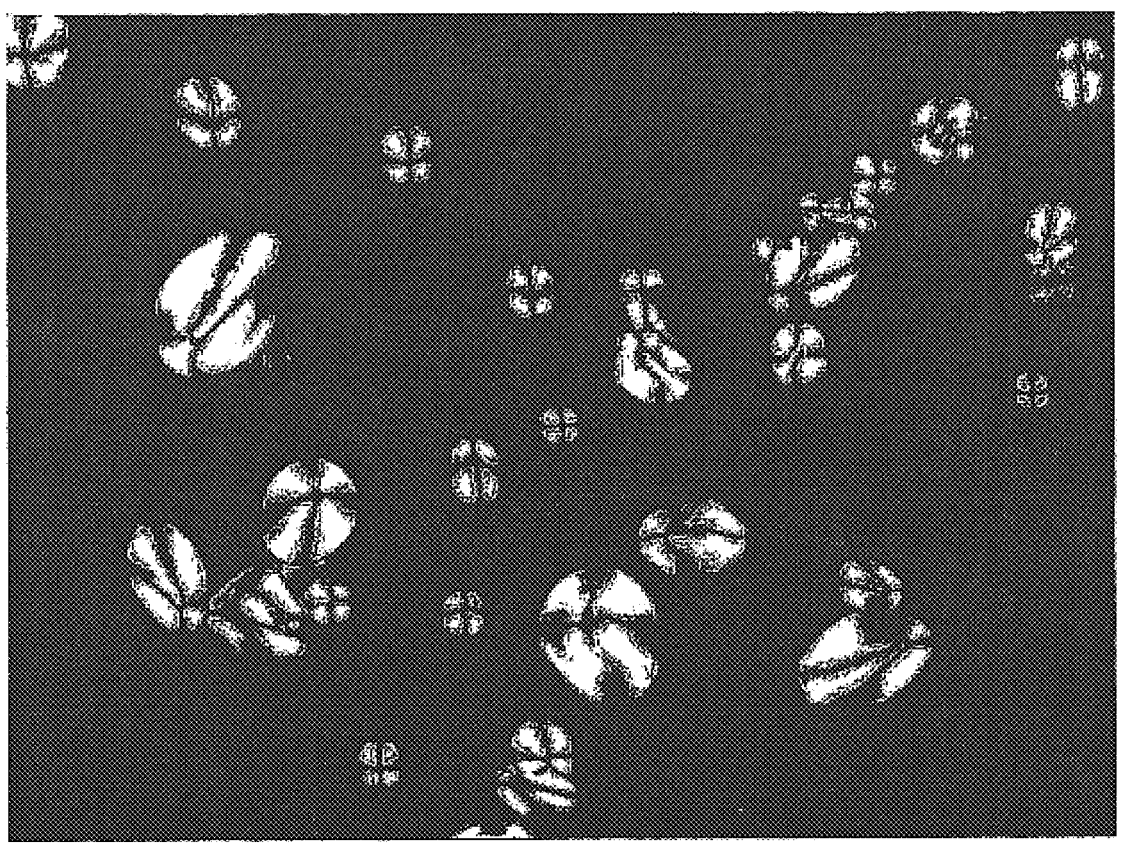
FIG. 1 of the drawings shows the crystalline structure (birefringence) of native potato starch under anhydrous conditions at 40 times magnification under polarized light.

The present invention relates to a starch based disintegrant for use in tablets, including direct compression, that will swell forcefully when exposed to water, while at the same time will not become soluble. To accomplish this we have found that starch must be physically processed to remove/destroy a portion of the native granular birefringence.

As used herein, the term starch is intended to include all granular starches and flours obtained from a plant source. Typical sources of starches and flours are cereals, tubers, roots, legumes and fruits. The native source includes, but are not limited to corn, pea, potato, sweet potato, banana, barley, wheat, rice, sago, amaranth, oat, tapioca, arrowroot, canna, sorghum, and waxy or high amylose varieties thereof. As used herein, the term "waxy" is intended to include a starch or flour containing at least about 95% by weight amylopectin and the term "high amylose" is intended to include a starch or flour containing at least about 40% by weight of amylose. While any starch can be useful in the practice of this invention, preferred base starches are those derived from corn, potato, tapioca, rice, sago and wheat with the most suitable being potato.

One preferred embodiment for starches of the current invention is that they are inhibited by methods know in the art. In cases where the processing step to remove/destroy a portion of the crystallinity involves shear (such as jet cooking or spray drying), it is necessary for the starch to be inhibited before processing. In some low shear processes, such as the solvent processes (described infra) inhibition is optional and may even be completely unnecessary.

Typical inhibiting reagents include, but are not limited to, sodium trimetaphosphate (STMP), epichlorohydrin, phosphorous oxychloride, glyoxal and polymeric versions of the above chemistries. Other types of non-chemical inhibition, including but not limited to heat treatment, heat/moisture treatment and physical processing, are also acceptable for use in this invention. Examples of heat/moisture treatments to produce inhibition are described in U.S. Pat. No. 3,578,497 (Hjermstad) and U.S. Pat. No. 5,725,676 (Chui et al.). Most suitable inhibitors for use in this invention are epichlorohydrin, phosphorous oxychloride and STMP.

The level of inhibition is important in high shear processes to control the amount of hydration (swelling) in the final product. Typical treatment levels will be chosen below 0.5 percent, most suitably between 0.001 and 0.1 percent based on the weight of starch.

The optimal inhibition chosen for each application will take into account possible interactions with active ingredients in the total formulation. The type and level of inhibition will depend greatly on the nature and parameters of the physical process, described infra, and offer the practitioner a wide range of choices to meet each application requirements.

In situations where inhibition of the starch is necessitated by the physical process, starches suitable for this invention will also be chemically modified.

In starches not requiring inhibition, chemical derivatization is completely optional. The modification can be either etherification or esterification and can be accomplished prior to, during, or after the inhibition step. The preferred modification is etherification using ethylene oxide or propylene oxide, most suitably propylene oxide. Modified starches of these types, and methods for making them, are described in "Starch: Chemistry and Technology", edited by R. L. Whistler et al, Chapter X, 1984.

One skilled in the art would recognize that the order of reaction would depend on the nature of the linkage and modification conditions. For example, inhibition with an esterifying reagent would preferably be accomplished after an etherifying reaction since the high pH required for the etherification would strip off some of the inhibition.

Once the starch has been inhibited and modified, a processing step is required to alter the crystallinity of the final product, thus making it swellable in cold water, while still maintaining very low solubility. We refer to the altered crystallinity (or birefringence), as being labile since it will disappear on addition of cold water (less than 50° C.).

Microscopic observation of native starch granules under polarized light shows a unique pattern (birefringence also known as Maltese crosses) which is caused by refraction of the light by the crystal structure. The crystals in the native starch granules act to hold the granular structure together. The presence of water at less than about 50° C. has no effect on the birefringence or granular structure. When the granules are heated in the presence of water above their gelatinization temperature the birefringence is irreversibly destroyed during the hydration and the starch molecules will become highly soluble.

The starches of this invention are characterized by an altered crystallinity that also provides birefringence in the dry state. Microscopic observation in the dry state under polarized light shows the Maltese crosses are somewhat irregular and different from the native granules, but still very distinct. Addition of cold water (less than 50° C.) to the granules of the present invention will cause rapid hydration and loss of the birefringence. Since the altered crystal state is now lost the hydration is accompanied by a forceful swelling without solubilizing the starch molecules. Starches without birefringence in the dry state have already begun to swell and will have diminished disintegrating power.

The processing step needed to alter the crystallinity can be accomplished under many conditions and in aqueous and non-aqueous media, but must afford a dry solid powder. Typically the process will involve heating a mixture of granular starch and water under conditions of time, temperature and pressure to facilitate partial reduction of the native granule's crystallinity. One skilled in the art would of course recognize that compounds such as solvents, sugars and salts could be used to manipulate the above parameters to accomplish the desired transformation.

One preferred method of preparing starches for this invention is the use of a solvent system with limited amounts of water present (low shear process). Typical solvents for this system would be C-1 to C-4 simple alcohols. Common examples of these materials are methanol, ethanol or isopropanol. The process involves suspending the starch (which could be native, modified, inhibited or modified and inhibited starch) in a water/alcohol mixture and heating to around the boiling point. Upon cooling the starch can be recovered by filtration and air-dried. Addition of a small amount of a suitable basic material can facilitate the process. Typically one percent or less of an alkaline earth or alkaline metal hydroxide (e.g. sodium hydroxide or potassium hydroxide) will be utilized in the solvent process.

An alternative method for preparing the starches containing labile crystalline structure of this invention is to utilize an aqueous salt solution in place of the solvent system described above. Examples of suitable salts are, but not limited to, sodium chloride, potassium chloride, sodium acetate, sodium sulfate and the like.

A preferred embodiment of this invention is utilizing spray drying to simultaneously remove some of the granular crystallinity and dry the product. It is preferred that the granular starches be inhibited when spray drying is used to make the processing more controllable. Spray drying of this type generally involves contacting the aqueous inhibited starch slurry with live steam for a very controlled period of time. This can be accomplished in special two fluid nozzles with various chamber designs that will allow for exact control of how much of the crystallinity is removed. For a thorough review of this technology see U.S. Pat. No. 4,600,472 (Pitchon et al.), U.S. Pat. No. 4,610,760 (Kirkpatrick et al.) and U.S. Pat. No. 5,149,799 (Rubens). Additionally, spray drying can be coupled with jet-cooking to afford a separate method for partially removing the granular crystallinity. The process for coupling the jet cooking and spray drying is detailed in U.S. Pat. No. 5,188,674 (Kasica et al.).

Spray drying can also be utilized in the more traditional sense to simply dry a product that has been previously treated to remove some of the crystallinity. Processes such as the solvent process, described above, or other aqueous processes for removing some of the crystallinity could be accomplished in a separate step and the dry powder recovered utilizing spray drying or other drying processes know in the art.

For the products of this invention to be useful as tablet disintegrants, a number of other criteria are necessary. First is low solubility in cold water. This parameter can be used as an indicator of whether the particles will become sticky when swollen in water. Highly soluble, sticky materials will not allow the tablet to readily fall apart. As used herein, low solubles is defined as less than about 5%, more suitably less than about 2% of the total starch dissolved in deionized (DI) water at 25° C.

For applications in which hot water (85° C.) is utilized, such as laundry detergents, suitable starches will have a solubility of less than 2% dissolved starch In DI water at 85° C.

Another advantage of the starches is their ability to rapidly swell from their original size on addition of water or aqueous salt solution. It is this swelling of the starch particles that is responsible for causing the tablet to rupture and disintegrate. To be effective as a super-disintegrant (used at 1% or less) it has been found that these products must swell at least about 200 percent on addition of water. Alternatively stated the starches of this invention must have a swelling ratio of at least 2.0 (hydrated volume/dry volume).

Additionally, the starch-based disintegrants suitable for use in this invention are characterized in that they have the same or smaller size and shape as the native starch from which they were derived. Preferably the average particle size will be no greater than the native granules from which it was derived. It is believed that the smaller size provides more uniform distribution of disintegrant particles throughout the tablet. Therefore, proper and uniform expansion forces needed for effective tablet disintegration are obtained at usage levels of equal to or less than one percent.

Yet another embodiment of the present invention is that these starch-based disintegrants swell to about the same extent in both water and physiological fluids. For the purposes of this application physiological fluids are defined as 0.1 N NaCl solution. To gauge the swelling effectiveness of starches in physiological fluids, a salt swelling ratio was defined as the swelling volume of a starch in 0.1 N NaCl divided by the swelling volume of the same starch in DI water. A suitable ratio for starch based disintegrants of this invention is defined as being equal to or greater than about 0.8.

Another property considered important for the starch based disintegrant in many applications is the disintegration time (time for a tablet to fall apart on contacted with water). While not all applications will require a rapid disintegration, typically a suitable disintegration time of less than about 300, most suitably 100 seconds is desired.

The disintegrants of this application are suitable for any tablet made by direct compression, dry compression, or wet granulation in which water is in a limited amount (such as a solvent system) so as not to hydrate the labile birefringence. Examples of such suitable tablets can be, but are not limited to, pharmaceuticals, vitamins, supplements, herbals, detergents, dishwasher detergents, agricultural and food type materials such as bouillon cubes and confections.

The following examples are offered to further illustrate the invention. They are not meant to limit the scope or spirit of the invention in any way. One skilled in the art will realize the wide latitude in starch types, cross-linkers and processing conditions available to practice this invention.

EXAMPLES

All percentages used herein are on a weight/weight basis unless otherwise noted. The following test procedures were used throughout the examples. For all the examples the control was carboxymethyl starch (sodium starch glycolate also known as EXPLOTAB®).

Analytical Procedures:

Swelling volume was evaluated using a sedimentation volume test (SVT). The samples were added at 1% solids into a 75 ml of solvating media, deionized (DI) water or 0.1N NaCl and mixed vigorously in the graduated cylinder. Any powder was rinsed off the walls of the cylinder with the appropriate solvating medium to the final volume of 100 ml. The sedimentation volume (ml/g) was determined after 24 h.

Solubility was determined using gravimetric method and a 2% dispersion of the test starch suspended in DI water. For low temperature testing, the solutions were prepared at 25° C. and for high temperature testing the solutions were prepared at 85° C. The sample was filtered or centrifuged to remove insoluble materials. The supernatant was mixed with a known amount of pre-dried sand and dried in an oven at 105° C. to the constant weight. This final weight minus the weight of the initial dry sand represented the total weight of the solubles.

Granule integrity and birefringence were evaluated using microscopy and polarized light microscopy, respectively. Samples were suspended in DI water or mineral oil at 1% solids. About 0.05 ml was placed on the microscopic slide. Evaluation in mineral oil served to evaluate powders in their anhydrous form to detect birefringence and granular structure. Samples were placed in water and then observed under the microscope using polarized light to see if the birefringence was lost and how much swelling (hydration) occurred.

Figure 2:
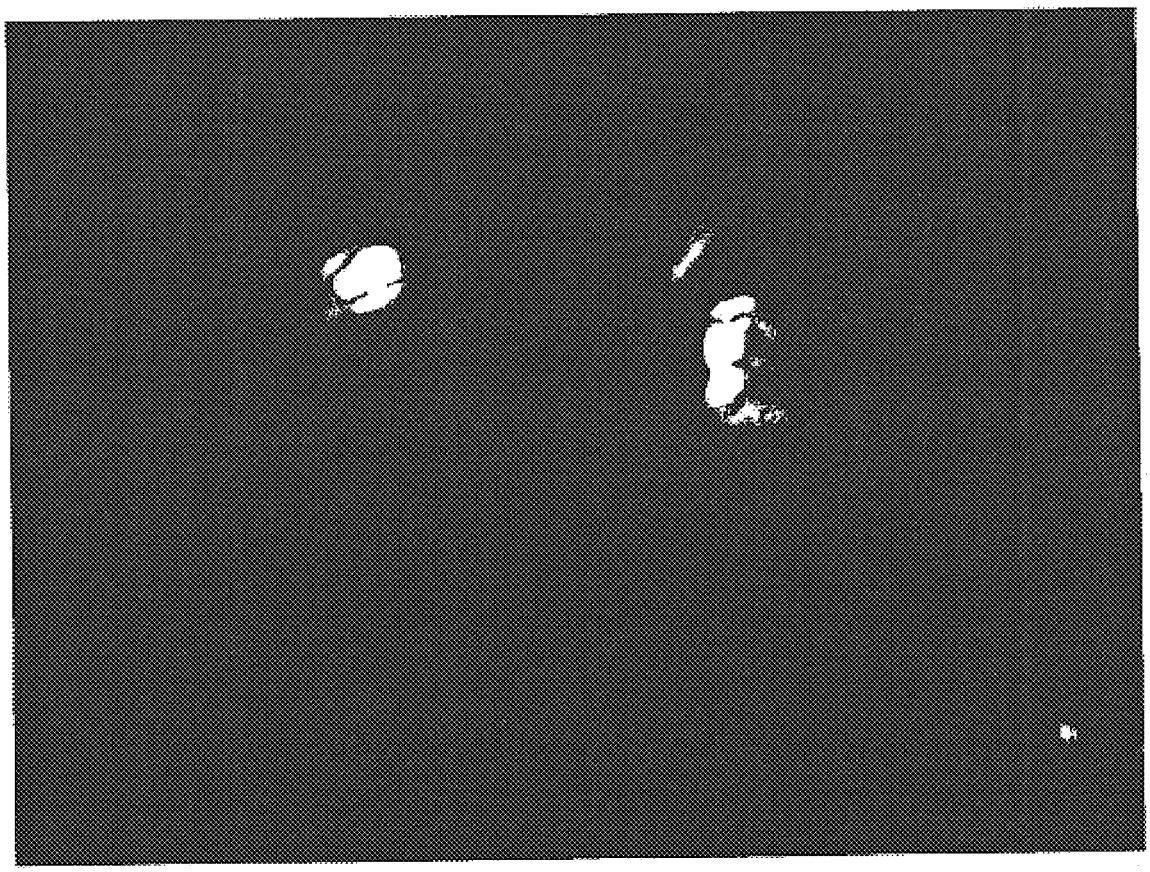
FIG. 2 of the drawings show the structure (lack of birefringence) of a pregelatinized (i.e. cooked) potato starch at 40 times magnification under anhydrous conditions and polarized light. This structure would be typical for the starches of the prior art.
Figure 3:
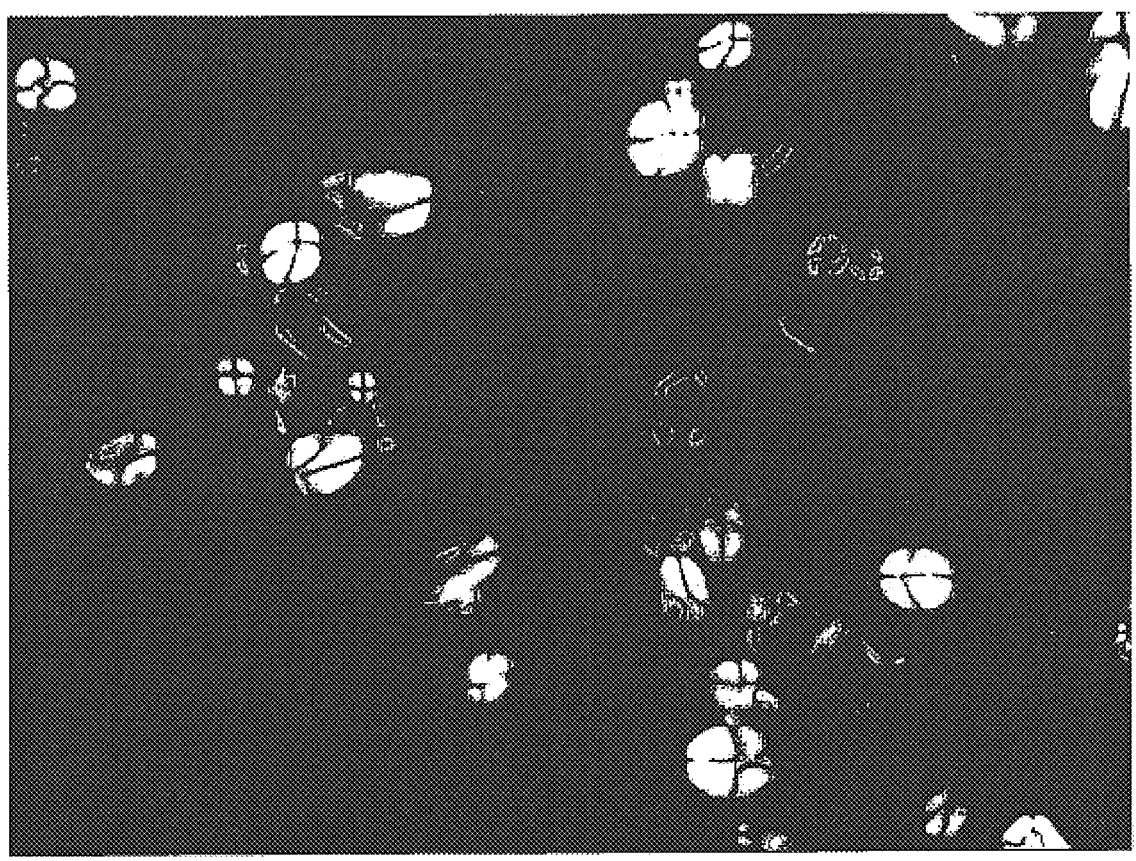
FIG. 3 of the drawings shows the altered crystalline state (slightly different birefringence) typical of the starches of this invention at 40 times magnification under anhydrous conditions and polarized light.

FIG. 1 show a typical potato starch at 40 times magnification in oil viewed under polarized light. The dark lines against the bright granular body are what are referred to as birefringence. FIG. 2 shows what a typical gelatinized starch sample looks like with the granular structure destroyed/damaged by cooking or modification. The structures in FIG. 2 are typically seen for starch disintegrants of the prior art. FIG. 3 shows the altered crystallinity of starches of this invention. The slightly different intensity and pattern of the birefringence are illustrative of starches possessing the labile crystalline structure. Addition of water to the starches of this invention will provide materials that are indistinguishable from those shown in FIG. 2.

Tablet Composition

All tablets were prepared using dicalcium phosphate as a filler, UNI-PURE® LD starch (National Starch and Chemical Company, Bridgewater N.J.) as an extragranular binder and magnesium stearate as a lubricant. Filler was mixed with starch samples, extragranular binder and samples were mixed for 20 min, then lubricant was added and samples were mixed for additional 30 s. Initially, super-disintegrants were evaluated at 4% or 1% of the total formulation, as stated.

Tableting

All tablets were prepared using 500 mg of powder on the single station tablet press, model MTCM-I (Globe Pharma, Inc.) at 13.7 MPa compression force. The tablet press was fitted with 1.27 cm diameter punch die. Tablet crushing strength was measured on a Dr. Scheuniger Pharmatron Model 6D Tablet Tester.

Disintegration Time

The tablets were tested in DI water at 37° C. using disintegration apparatus (Erweka Model ZT1) for a maximum time of 3600 s. The time required to achieve complete tablet disintegration was measured.

Example 1

Preparation of a Potato Based Super Disintegrant

Chemical Modification of Potato Starch:

Potato starch was added into 25% sodium sulfate solution to achieve 40% (w/w) slurry. The temperature of the slurry was increased to 40° C., pH was adjusted to 11–11.5, and chemical modification reagent 2, 4, 6, or 8% propylene oxide, was added. The reaction was carried for 18 h at 40° C. The starch was then neutralized to pH of 5.5–6.0 with 3N HCl, filtered, washed, and recovered by air drying.

Chemical Inhibition of Potato Starch:

The potato starch from above was added into 0.003% sodium chloride solution to achieve 40% (w/w) slurry. The pH of the slurry was adjusted to 11–11.5 and an appropriate amount of inhibiting reagent, 0.085, 0.093, 0.1 or 0.24% phosphorus oxychloride was added. The reaction was carried out for 30 min at room temperature, then pH was adjusted to neutral with 3N HCl. The starch was filtered, washed, and recovered by air drying. The results of substitution and inhibition are shown in Tables 1 and 2, below, and all experimental samples were prepared by spray drying using the procedure described in example 3a.

TABLE 1

Effect of crosslinking and substitution on potato starch disintegrants (1% disintegrant level)

| Treatment | Inhibition | Disintegration Time (s) | Swelling Volume $H_2O$ (ml/g) | Solubility @ 25° C. (%) | Solubility @ 85° C. (%) |
|---|---|---|---|---|---|
| Control | | 105 ± 23 | 33 | 13 | >20 |
| 4% propylene oxide | 0.093% $POCl_3$ | 92 ± 4 | 9 | <2 | — |
| 6% propylene oxide | 0.085% $POCl_3$ | 95 ± 5 | 10 | <1 | <2 |
| 6% propylene oxide | 0.24% $POCl_3$ | 74 ± 3 | 8 | <1 | — |

TABLE 2

Effect of substitution on potato starch disintegrant (1% disintegrant level)

| Treatment | Inhibition | Disintegration Time (s) | Swelling volume DI $H_2O$ (ml/g) | Swelling Volume 0.1 N NaCl (ml/g) | Solubility @ 25° C. (%) |
|---|---|---|---|---|---|
| Control | | 105 ± 23 | 33 | 16 | 13 |
| 8% propylene oxide | 0.1% $POCl_3$ | 79 ± 4 | 13 | 11 | <2 |
| 6% propylene oxide | 0.1% $POCl_3$ | 90 ± 3 | 10 | 9 | |
| 4% propylene oxide | 0.1% $POCl_3$ | 84 ± 4 | 10 | 8 | |
| 2% propylene oxide | 0.1% $POCl_3$ | 86 ± 3 | 8 | 8 | |
| 3% acetic anhydride | 0.1% $POCl_3$ | 283 ± 21 | 9 | 9 | <2 |

Example 2

Preparation of a Labile Birefringent Starch Granule Using an Alcohol Process 100 g of the potato starch from above is suspended into 200 ml of an aqueous methanol (70/30 alcohol/water) solution and brought to a boil by heating in a steam bath. The product was boiled for 30 minutes and then allowed to cool to room temperature. The starch was recovered by filtration and then allowed to air dry.

Example 3a

Preparation of a Labile Birefringent Starch by Spray Drying

One Step Process

Spray drying was performed on a Niro Spray Dryer with a two fluid nozzle. The starch as prepared in Example 1 was slurried at 20–30% (w/w) solids in water and was introduced directly into the nozzle with the feed pressure of 20.6–24.0 MPa. In the nozzle, the slurry was coming in contact with steam at 0.8–1.2 MPa. Slurry solids, pumping rate, length of the nozzle, steam pressure, and back pressure in the nozzle were manipulated to accomplish desired degree of starch pregelatinization while maintaining granule integrity and partial birefringence. Results are shown in table 3 and 4, below.

Example 3b

Preparation of a Labile Birefringent Starch by Coupled Jet-cooking/spray Drying The coupled jet-cooking and spray-drying was performed as described in the patent U.S. Pat. No. 5,131,953. The process was accomplished at 20–30% starch solids (obtained from Example 1, above) and low steam pressure. The conditions were designed to generate high solids and low shear environment to achieve partial starch cooking and labile/residual birefringence. The starch slurry was subjected to 80–85° C. cooking temperature. The steam pressure to the cooking chamber and line pressure to the spray drier were maintained at 0.7 MPa.

TABLE 3

Potato starch disintegrant - effect of type of processing. (1% distintegrant level)

| Treatment/ inhibition | Processing Step | Disintegration Time (s) | Swelling DI $H_2O$ (ml/g) | Swelling 0.1 N NaCl (ml/g) | Solubility @ 25° C. (%) |
|---|---|---|---|---|---|
| Control | | 105 ± 23 | 33 | 16 | 13 |
| None/none (native potato) | Drum dried | 1367 ± 11 | 85 | Not measured | 14 |
| 8% propylene oxide/ 0.1% $POCl_3$ | Spray dried[2] | 79 ± 4 | 13 | 11 | <0.5 |
| 8% propylene oxide/ 0.1% $POCl_3$ | Jet cooked/ Spray dried[3] | 93 ± 10 | 11 | 9 | <0.5 |

[2] = Prepared by the method described in example 3a
[3] = Prepared by the method described in example 3b

TABLE 4

Effect of processing conditions on disintegration time
(1% disintegrant level)

| Treatment/ Inhibition | Process | Processing Variables Nozzle Configuration | Disintegration Time (s) | Swelling DI H$_2$O (ml/g) | Solubility @ 25° C. (%) |
|---|---|---|---|---|---|
| Control | | NA | 105 ± 23 | 33 | 13 |
| 4% propylene oxide/0.093% POCl$_3$, | Spray drying[2] | ³⁄₁₆ aperture, 2 spacers | 92 ± 4 | 9 | <2 |
| | | ⅜ aperture, no spacers | 300 ± 15 | 4 | <0.5 |
| 8% propylene oxide/ 0.1% POCl$_3$ | Spray drying[2] | 2 mm/1 fluid nozzle | 79 ± 4 | 13 | <2 |
| | | 120SS/2 fluid nozzle | 160 ± 5 | 6 | <0.5 |
| 8% propylene oxide/ 0.1% POCl$_3$ | Spray drying coupled with jet-cooking[3] | Steam valve 7.5%, back pressure 0.9 MPa, steam line 0.6 MPa | 93 ± 10 | 11 | <0.5 |
| | | Steam valve 25%, back pressure 1.1 MPa, steam line 1.0 MPa | 248 ± 13 | 14 | <0.5 |

[2]= Prepared by the method described in example 3a
[3]= Prepared by the method described in example 3b

Example 3c

Preparation of a Labile Birefringent Starch by Thermal Inhibition Followed by Spray Drying A sample of NOVATION® 1600 starch (a thermally inhibited potato starch available from National Starch and Chemical Co., Bridgewater, N.J.) is slurried at 20–30% (w/w) solids in water and is introduced directly into the nozzle with the feed pressure of 20.6–24.0 MPa. In the nozzle, the slurry is coming in contact with steam at 0.6–0.8 MPa. Slurry solids, pumping rate, length of the nozzle, steam pressure, and back pressure in the nozzle are manipulated to accomplish desired degree of starch pregelatinization while maintaining granule integrity and partial birefringence.

Example 3d

Preparation of a Labile Birefringent Starch by Spray Drying

Two Step Process

A slurry of starch is prepared by adding 2500 g of starch to 7500 g of water and mixing until uniform. The slurry is then heated to at or below the gelatinization temperature and held for 2–30 minutes. The slurry is then cooled to stop gelatinization and then pumped into a Niro spray drier with a single fluid nozzle fed at 20.6–24.0 MPa. The chamber temperature is held between 75 and 125° C. to dry the product without destroying the residual crystalline structure.

Example 4

Preparation of a Labile Birefringent Starch by Flash Drying

A slurry of starch is prepared by adding 2500 g of starch to 7500 g of water and mixing until uniform. The slurry is then heated to about the gelatinization temperature and held for 2–30 minutes. The slurry is then cooled to stop gelatinization and then water is removed by flash drying.

Example 5

Preparation of Tablet Disintegrant in Salt Solution

A total of 40 grams of sodium sulfate is dissolved in 200 ml of water. To this solution 100 grams of potato starch is mixed until uniform. The slurry is then heated in a water bath at 80° C. for 20 minutes. The slurry is then cooled to room temperature and filtered. The starch cake is washed with 70/30 ethanol/water mix to remove the residual salt. The starch is air dried to less than 10% moisture.

Example 6

Measurement of Particle Size

Evaluation of particle size was performed using two methods: sieving and optical microscopy. In the sieving method, sieves with the U.S. mesh numbers of 120, 170, and 400 were used. 100 g of each powder was placed on the top sieve and tapped for 30 min. The weight retained on each sieve and a pan was determined. Additionally, the samples were evaluated in a non-aqueous medium under the microscope, and particle size was measured directly. Results are shown in table 5, below.

TABLE 5

Particle size of potato starch before and after modification and spray-drying

| Treatment/inhibition | Process | Particle size (μm) | Distribution (%) |
|---|---|---|---|
| None/none (native potato) | none | 124–88 | 0.07 |
| | | 87–37 | 41.4 |
| | | <37 | 55.9 |
| 4% Propylene oxide/ 0.085% POCl$_3$ | none | 124–88 | 7.9 |
| | | 87–37 | 31.2 |
| | | <37 | 51.3 |

TABLE 5-continued

Particle size of potato starch before and after modification and spray-drying

| Treatment/inhibition | Process | Particle size (μm) | Distribution (%) |
|---|---|---|---|
| 4% Propylene oxide/ 0.085% POCl$_3$ | Spray dried[2] | 124–88 87–37 <37 | 0.03 13.1 86.6 |

[2]= prepared by the process describe in example 3a

The results from the above examples show the utility and versatility of starches that are inhibited and processed to remove a portion of their native crystallinity. The effective utilization of starch type, inhibition type and level and processing conditions in the preparation of a highly efficient starch based tablet disintegrant is what this application offers the practitioner.

What is claimed is:

1. A starch based tablet disintegrant comprising a starch characterized by having cold water solubles of less than 2%, a swelling ratio of at least 2 (hydrated volume/dry volume), a salt swelling ratio of greater than 0.8, birefringence which disappears on addition of water at 50° C. and has an average particle size no greater than the native starch from which it was prepared.

2. The disintegrant of claim 1 wherein the starch is chosen from the group consisting of corn, potato, tapioca, sago, wheat and rice.

3. The disintegrant of claim 2 wherein the starch is modified with propylene oxide or ethylene oxide.

4. The disintegrant of claim 2, wherein the starch is inhibited.

5. The disintegrant of claim 4, wherein the starch is inhibited with a reagent chosen from the group consisting of sodium trimetaphosphate, phosphorus oxychloride and epichlorohydrin.

6. The disintegrant of claim 4, wherein the inhibition is obtained by a heat/moisture treatment.

7. The disintegrant of claim 4, wherein the starch is modified with propylene oxide and inhibited with phosphorus oxychloride.

8. A tablet comprising a starch of claim 1.

9. The tablet of claim 8, wherein the starch is modified.

10. The tablet of claim 8, wherein the starch is modified and inhibited.

11. The tablet of claim 10, wherein the starch crystallinity has been altered by spray drying.

12. The tablet of claim 10, wherein the starch concentration is at or below 1%.

13. A tablet comprising a disintegrant, wherein the disintegrant consists essentially of the starch of claim 1.

14. A tablet comprising a disintegrant, wherein the disintegrant consists essentially of the starch of claim 7.

15. A starch characterized by having hot water solubles of less than 2% at 85° C., a swelling ratio of at least 2 (hydrated volume/dry volume), a salt swelling ratio of greater than 0.8 and birefringence which disappears on addition of water at 50° C. and has an average particle size no greater than the native starch from which it was prepared.

16. A tablet comprising the starch of claim 15.

17. An inhibited, chemically modified starch characterized by having cold water solubles of less than 2%, a swelling ratio of at least 2 (hydrated volume/dry volume), a salt swelling ratio of greater than 0.8, birefringence which disappears on addition of water at 50° C. and has an average particle size no greater than the native starch from which it was prepared.

* * * * *